Dec. 17, 1957 J. J. GRULLEMANS Plant Pat. 1,670
HEMEROCALLIS PLANT
Filed Jan. 14, 1957
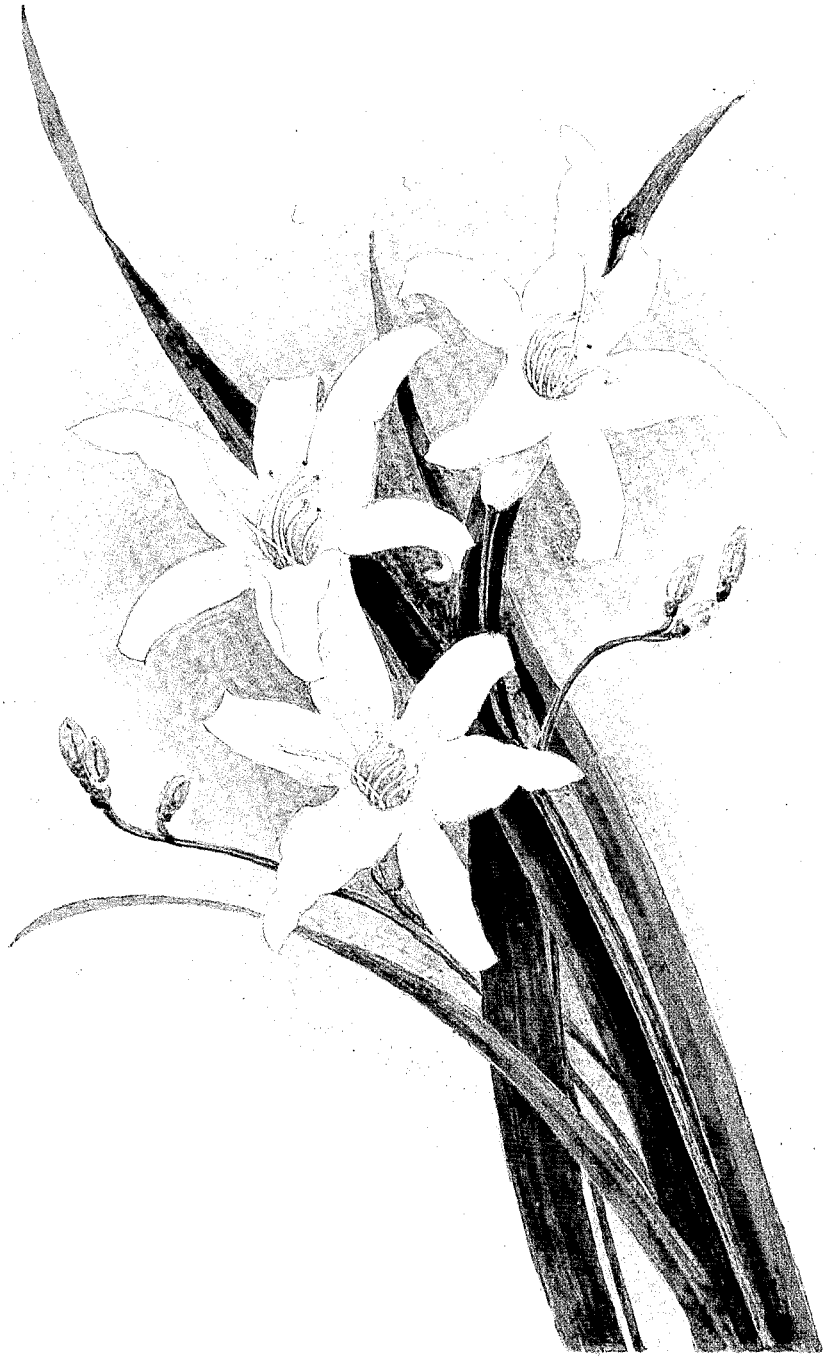
WITNESS
Addison E. Avery
INVENTOR
John J. Grullemans,
by John H. Leonard,
his ATTY.

United States Patent Office

Plant Pat. 1,670
Patented Dec. 17, 1957

1,670

HEMEROCALLIS PLANT

John J. Grullemans, Harwichport, Mass.

Application January 14, 1957, Serial No. 634,136

1 Claim. (Cl. 47—60)

This invention relates to a new and distinct hybrid Hemerocallis plant.

The new plant is illustrated in the drawing in which are shown a number of typical stems, blooms, buds, and leaves.

I obtained the seeds for the plant by crossing, as the parents, two unnamed Hemerocallis plants, each of which was a seedling. I obtained the seeds, from which the parents were produced, from unnamed hybrids which I had selected for color and which I was then growing specifically for breeding purposes in an experimental plot. I carefully controlled the pollination, and other factors affecting the growth, of the parent plants. I planted the seeds produced by the crossing of these parents and selected one of the resultant seedlings, which grew to become the present plant.

The plant was first asexually reproduced by me at Mentor, Ohio by plant division.

The root system of the plant is the usual tuberous to fibrous mass which is common for Hemerocallis plants, and is of the average size.

It has good resistance to wetness and drouth. Their winter resistance is good, both protected and unprotected. The plants have been grown without root damage in an open test field without protection for four years at Mentor, Lake County, Ohio, at a period during which the lowest temperature recorded was approximately 10° below zero, Fahrenheit.

Since the development of the plant, the roots have not been attacked by disease or insect pests.

The roots thrive well in a wide range of soils.

The exposed part of the plant is herbaceous and hardy. Its general growth is upright and spreading and, when fully grown, it is generally dense or compact. It has the average height and spread for a three-year old Hemerocallis plant which has been field grown. It is generally in the form of a symmetrical clump, rounded at the top.

The plant is vigorous in growth. It withstands both drouth and wet seasons, and withstands low temperatures well, both protected and unprotected. The exposed portions of the plant have not been attacked by any diseases or insects.

For the best growth, it prefers conditions varying from intense sunlight to partial shade and rather moist soil. It appears to grow well in any of the soils ordinarily found in yards and gardens.

The main stalks or stems of the plant are curving and of the usual length, stiffness and toughness. They are generally adequate to support the bloom and fruit well. The stems are of the usual color and surface texture.

The plant has floral branches of the usual surface texture and quantity, alternately arranged. They are stiff but rather flexible so that they support the bloom and fruit well. They are of the usual length for a Hemerocallis plant.

The color of the stems varies from a Peridot Green, comparable to Maerz and Paul Plate 22–L–6, to a green comparable to Maerz and Paul Plate 22–L–8, with some yellow. The color is relatively uniform.

The foliage is dense and compact.

The leaves are basal and abundant and of the average size, length and width. They are linear from the base with entire margins and taper in the usual manner. They are of the average thickness and texture. Their persistency on the plant is good.

The plant produces an abundance of blooms of high quality throughout a geographical range in the United States from the east coast to the west coast with but very few exceptions and from Canada as far south as Florida. It produces the best blooms in the more temperate climates, however. The blooms produced in full sunlight appear to be somewhat brighter than those produced in partial shade, although an abundance of high quality blooms are produced in the partial shade.

The best blooms are produced in a temperate moist season, in a rich soil which varies from moist to damp and from slightly acid to neutral.

The quantity of the blooms are slightly reduced only if variations from the above normal ranges of conditions are very extreme.

The colors of the plant and blooms are little affected by the growing conditions unless they become quite extreme.

The plant blooms continuously throughout late July and all of August.

The buds are of medium size and plump, and are of the usual elongated shape for Hemerocallis plants. Their aspect is smooth and more or less waxy. They are borne generally upright on terminals of the stems. Their colors, based on the British Colour Council Horticultural Colour Charts, ranges from Apricot, Plates 609 to 609/1, during the periods when the sepals first divide, when the petals begin to unfurl, and when the buds are half blown.

The sepals and calyx are of the usual size, shape and texture for Hemerocallis plants.

The peduncles vary in length from forty-two to forty-eight inches, and have the usual texture and color. They are very strong.

The pedicels or individual flower stalks average from three to five inches in length and have the usual texture and color. They, too, are strong.

The blooms range in size from about three and a quarter to three and a half inches in diameter. The average number of blooms at any given time within the blooming period ranges from fifteen to thirty or more for a single plant. They are borne in scapes of three to ten blooms each. They have the usual permanence when on the plant and when cut.

The color of the blooms, based on the British Colour Council Horicultural Colour Charts, ranges from a Saturn Red, Plates 13 to 13/1, streaked with tones of Nasturtium Orange, Plates 610 to 610/2, to Apricot, Plates 609 to 609/3. The colors are generally most pronounced near the center of the blooms.

At the outer edges and tips of the petals, the color is generally an Egyptian Buff, Plates 407 to 407/3 and, in some instances, ranges to Ivory White. At their bases, the petals are generally Saturn Red, range to Apricot, Plate 609. The inside of the petals, from the base of the petals and the band, almost to the tips, is of the Saturn Red blending to the Egyptian Buff and to Ivory White on the outer edges. The reverse of the petals ranges from Apricot, Plate 609/3 to Egyptian Buff, Plate 407/3.

The general tonality of the blooms of the plant from a distance ranges from Apricot, Plate 609/3 to the Egyptian Buff, with the apricot predominating. There is little change in the color during the blooming season.

The petals are of the usual texture, form and arrangement, being distinguished only by their color. The same is true of the blooms as a whole.

The bloom has a fragrance of the usual strength and quality.

The stamens range from Apricot, Plate 609 to Egyptian Buff 407/3, including a Nasturtium Orange, comparable to Plates 610 to 610/2. They are present in the usual quantity of six to the bloom.

The filaments are relatively long and likewise range in color from Apricot, Plate 609, to Egyptian Buff. They have whitish tips.

There is one long pistil which is also a Nasturtium Orange, except at the end which is an ivory color.

The fruit or seeds, in general, are usual for a Hemerocallis plant. They are borne in the usual manner of grouped bracts on scapes.

The outstanding feature of the plant is the unusual color of the blooms which is not found in blooms of other Hemerocallis plants.

Having shown and described my new variety of Hemerocallis plant and its mode of asexual reproduction, I claim:

The new and distinct variety of Hemerocallis plant as described and illustrated, distinguished particularly by the color of its blooms.

No references cited.